United States Patent
Schumacher et al.

(12)

(10) Patent No.: US 6,190,906 B1
(45) Date of Patent: Feb. 20, 2001

(54) EXPRESSION VECTOR FOR THE REGULATABLE EXPRESSION OF FOREIGN GENES IN PROKARYOTES

(75) Inventors: Günther Schumacher, Bernried; Michael Jarsch, München; Winfried Boos, Constance, all of (DE)

(73) Assignee: Roche Diagnostics GmbH, Mannheim (DE)

( * ) Notice: Under 35 U.S.C. 154(b), the term of this patent shall be extended for 0 days.

(21) Appl. No.: 07/300,357

(22) Filed: Jan. 23, 1989

(30) Foreign Application Priority Data

May 20, 1987 (DE) ................................. 37 16 957
May 19, 1988 (WO) .................... PCT/EP88/00446

(51) Int. Cl.[7] ............................ C12N 15/63; C12N 15/00; C07H 21/04
(52) U.S. Cl. .................... 435/320.1; 435/69.1; 435/69.8; 435/71.2; 536/23.1; 536/24.1
(58) Field of Search .............................. 435/320.1, 69.1, 435/71.2, 69.8, 172.3; 935/41, 43, 48; 536/23.1, 24.1

(56) References Cited

U.S. PATENT DOCUMENTS 4,711,843 * 12/1987 Chang .................................. 435/69.1

OTHER PUBLICATIONS

Waye et al. NAR 13:8561–8571(1985). Citadon p. 18 of the instant specification.*
Yanish–Persson Gene 33:103–119(1985). Citadon p. 17 of the instant specification.*
Maniatis et al. Molecular Cloning: a laboratory manual, CHSL, Cold Spring Harbor, New York, 1982, p. 422.*
Scripture, J. Biol. Chem. 258: 10853–10855 (1983).*
Kendall, Nature 321: 706–708 (1986).*
Muller et al. (1985), J. Bacteriol., vol. 163, pp. 37–45.*
Gascuel et al. (1986), J. Mol. Evol., vol. 24, pp. 130–142.*

* cited by examiner

*Primary Examiner*—Robert A. Schwartzman
*Assistant Examiner*—Andrew Wang
(74) *Attorney, Agent, or Firm*—Fulbright & Jaworski L.L.P.

(57) ABSTRACT

The invention provides an expression vector useful in expressing foreign genes in procaryotes. The vector consists of the promotor/operator region and initiation point of translation of the mgl operon. This combination is referred to as a regulation sequence. In order to prepare this, desired portions of the mgl operon are cut from the genome of a cell which can utilize galactose via appropriate restriction endonucleases. This is then inserted into a DNA vector.

14 Claims, 11 Drawing Sheets

```
        EcoRI
  1  GAATTCGCCGCGTTCGAACTGCATATCCTGAAGCGTCCGGGAGCAGAAGCCGACTATACG

61  GCAGAAGAGATTGCTCAGGCAGAGCGGCGTTTCGCCACCATGAGCGAGGAAGACAAAGCA

121  CGTCTGACCCGCAACATTATTGCCGGTTTACCTGGTACGGCGCCATTCGGTGGCATGGCG

181  ACAGAATGCGGTACTGATCACTAACTGATTACGCACCGCATGTAACCGTTTTCAATCTGT

241  GAGTAAATTCACAGTTTATTAACATTGTGATAGCTATGATGACAACGTTTGTCGCACTGT

301  AACTAACGTGTAACAGTTAGTTGTCAGTTTTGCTGGGGTATTTCGCTTATAAAAACCGTT

361  ATCACAATATCCCGCGACTACCGGACAAAAATAAAGAGTTGAATAAGAGCTTATCCCATT

421  AGGGCTATTTTACTTGCCATTTTGGACCTGGGCAGTGCTCGCCAAAACGCGTTAGCGTTT

481  TGAACGCGCTAGCGGCGGCCCGAAGGGCGAGCGTAGCGAGTCAAACCTCACGTACTACGT

541  GTACGCTCCGGTTTTTGCGCGCTGTCCGTGTCCAAACTGCTGCGCCAATAACGCCTGGTG

601  GGATAGGCTCTAAATACGCTTCGGCGTTCAGTAACACGCGTTAACGTGCTGAACAGCCGG

661  GCATTTTTTTACGCTATACCCTACATAATAAAACCGGAGCTACC mglB-

705  ATGAATAAGAAGGTACTGACCCTTTCTGCCGTGATGGCAAGTCTGTTATTCGGCGCGCAC
     MetAsnLysLysValLeuThrLeuSerAlaValMetAlaSerLeuLeuPheGlyAlaHis

765  GCGCACGCG
     AlaHisAla

774  GCTGATACTCGTTGAAGCGGCGCACGAAAAACGCGAAAGCGTTTCACGATAAATGCGAAA

834  ACTTTAGCTTTCGCGCTTCAAATGAAACAGATGTATTAATTACTGCTTTTTATTCATTAC

894  ATGGGGATCC
           BamHI
```

FIG. 1 pUC18

```
   1 GCGCCCAATACGCAAACCGCCTCTCCCCGCGCGTTGGCCGATTCATTAATGCAGCTGGCA
  61 CGACAGGTTTCCCGACTGGAAAGCGGGCAGTGAGCGCAACGCAATTAATGTGAGTTAGCT
 121 CACTCATTAGGCACCCCAGGCTTTACACTTTATGCTTCCGGCTCGTATGTTGTGTGGAAT
 181 TGTGAGCGGATAACAATTTCACACAGGAAACAGCTATGACCATGATTACGAATTCGAGCT
 241 CGGTACCCGGGGATCCTCTAGAGTCGACCTGCAGGCATGCAAGCTTGGCACTGGCCGTCG
 301 TTTTACAACGTCGTGACTGGGAAAACCCTGGCGTTACCCAACTTAATCGCCTTGCAGCAC
 361 ATCCCCCTTTCGCCAGCTGGCGTAATAGCGAAGAGGCCCGCACCGATCGCCCTTCCCAAC
 421 AGTTGCGCAGCCTGAATGGCGAATGGCGCCTGATGCGGTATTTTCTCCTTACGCATCTGT
 481 GCGGTATTTCACACCGCATATGGTGCACTCTCAGTACAATCTGCTCTGATGCCGCATAGT
 541 TAAGCCAGCCCCGACACCCGCCAACACCCGCTGACGCGCCCTGACGGGCTTGTCTGCTCC
 601 CGGCATCCGCTTACAGACAAGCTGTGACCGTCTCCGGGAGCTGCATGTGTCAGAGGTTTT
 661 CACCGTCATCACCGAAACGCGCGAGACGAAAGGGCCTCGTGATACGCCTATTTTTATAGG
 721 TTAATGTCATGATAATAATGGTTTCTTAGACGTCAGGTGGCACTTTTCGGGGAAATGTGC
 781 GCGGAACCCCTATTTGTTTATTTTTCTAAATACATTCAAATATGTATCCGCTCATGAGAC
 841 AATAACCCTGATAAATGCTTCAATAATATTGAAAAAGGAAGAGTATGAGTATTCAACATT
 901 TCCGTGTCGCCCTTATTCCCTTTTTTGCGGCATTTTGCCTTCCTGTTTTTGCTCACCCAG
 961 AAACGCTGGTGAAAGTAAAAGATGCTGAAGATCAGTTGGGTGCACGAGTGGGTTACATCG
1021 AACTGGATCTCAACAGCGGTAAGATCCTTGAGAGTTTTCGCCCCGAAGAACGTTTTCCAA
1081 TGATGAGCACTTTTAAAGTTCTGCTATGTGGCGCGGTATTATCCCGTATTGACGCCGGGC
1141 AAGAGCAACTCGGTCGCCGCATACACTATTCTCAGAATGACTTGGTTGAGTACTCACCAG
1201 TCACAGAAAAGCATCTTACGGATGGCATGACAGTAAGAGAATTATGCAGTGCTGCCATAA
1261 CCATGAGTGATAACACTGCGGCCAACTTACTTCTGACAACGATCGGAGGACCGAAGGAGC
1321 TAACCGCTTTTTTGCACAACATGGGGGATCATGTAACTCGCCTTGATCGTTGGGAACCGG
1381 AGCTGAATGAAGCCATACCAAACGACGAGCGTGACACCACGATGCCTGTAGCAATGGCAA
1441 CAACGTTGCGCAAACTATTAACTGGCGAACTACTTACTCTAGCTTCCCGGCAACAATTAA
1501 TAGACTGGATGGAGGCGGATAAAGTTGCAGGACCACTTCTGCGCTCGGCCCTTCCGGCTG
1561 GCTGGTTTATTGCTGATAAATCTGGAGCCGGTGAGCGTGGGTCTCGCGGTATCATTGCAG
1621 CACTGGGGCCAGATGGTAAGCCCTCCCGTATCGTAGTTATCTACACGACGGGGAGTCAGG
1681 CAACTATGGATGAACGAAATAGACAGATCGCTGAGATAGGTGCCTCACTGATTAAGCATT
1741 GGTAACTGTCAGACCAAGTTTACTCATATATACTTTAGATTGATTTAAAACTTCATTTTT
1801 AATTTAAAAGGATCTAGGTGAAGATCCTTTTTGATAATCTCATGACCAAAATCCCTTAAC
1861 GTGAGTTTTCGTTCCACTGAGCGTCAGACCCCGTAGAAAAGATCAAAGGATCTTCTTGAG
1921 ATCCTTTTTTTCTGCGCGTAATCTGCTGCTTGCAAACAAAAAAACCACCGCTACCAGCGG
1981 TGGTTTGTTTGCCGGATCAAGAGCTACCAACTCTTTTTCCGAAGGTAACTGGCTTCAGCA
2041 GAGCGCAGATACCAAATACTGTCCTTCTAGTGTAGCCGTAGTTAGGCCACCACTTCAAGA
2101 ACTCTGTAGCACCGCCTACATACCTCGCTCTGCTAATCCTGTTACCAGTGGCTGCTGCCA
2161 GTGGCGATAAGTCGTGTCTTACCGGGTTGGACTCAAGACGATAGTTACCGGATAAGGCGC
2221 AGCGGTCGGGCTGAACGGGGGGTTCGTGCACACAGCCCAGCTTGGAGCGAACGACCTACA
2281 CCGAACTGAGATACCTACAGCGTGAGCTATGAGAAAGCGCCACGCTTCCCGAAGGGAGAA
2341 AGGCGGACAGGTATCCGGTAAGCGGCAGGGTCGGAACAGGAGAGCGCACGAGGGAGCTTC
2401 CAGGGGGAAACGCCTGGTATCTTTATAGTCCTGTCGGGTTTCGCCACCTCTGACTTGAGC
2461 GTCGATTTTTGTGATGCTCGTCAGGGGGCGGAGCCTATGGAAAAACGCCAGCAACGCGG
2521 CCTTTTTACGGTTCCTGGCCTTTTGCTGGCCTTTTGCTCACATGTTCTTTCCTGCGTTAT
2581 CCCCTGATTCTGTGGATAACCGTATTACCGCCTTTGAGTGAGCTGATACCGCTCGCCGCA
2641 GCCGAACGACCGAGCGCAGCGAGTCAGTGAGCGAGGAAGCGGAAGA
```

FIG. 7

EndoH-Gen

```
        EcoRI
    1   GAATTCCTCACTCATTAGGCACCCCAGGCTTTACACTTTATGCTTCCGGCTCGTATAATG

61   TGTGGAATTGTGAGCGGATAACAATTTCACACAGGAAACAGGCCATGTTCACTCCGGTTC

121   GCAGAAGGGTGCGGACGGCTGCGCTCGCGCTCTCGGCCGCCGCGGCCCTCGTCCTCGGTT

181   CCACCGCCGCGAGCGGCGCGTCAGCGACCCCCTCACCCGCTCCGGCCCCGGCCCCGGCCC
                                                              SphI
  241   CGGTGAAGCAGGGGCCGACCTCGGTGGCCTACGTCGAGGTGAACAACAACAGCATGCTCA

301   ACGTCGGCAAGTACACCCTGGCGGACGGAGGCGGCAACGCCTTCGACGTAGCCGTGATCT

361   TCGCGGCGAACATCAACTACGACACCGGCACGAAGACGGCCTACCTGCACTTCAACGAGA

421   ACGTGCAGCGCGTCCTTGACAACGCTGTCACGCAGATACGGCCGTTGCAGCAACAGGGCA

481   TCAAGGTCCTCCTCTCGGTGCTCGGCAACCACCAGGGCGCCGGGTTCGCGAACTTCCCCT

541   CACAGCAGGCGGCTTCGGCGTTCGCGAAGCAGCTCTCGGACGCCGTGGCGAAGTACGGCC
                SalI
  601   TCGACGGCGTCGACTTCGACGACGAATACGCCGAGTACGGCAACAACGGCACCGCGCAGC

661   CCAACGACAGTTCGTTCGTGCACCTGGTGACGGCACTGCGCGCGAACATGCCCGACAAGA
                                                              SalI
  721   TCATCAGCCTCTACAACATCGGCCCGGCCGCGTCCCGCCTGTCGTACGGCGGTGTCGACG

781   TCTCCGACAAGTTCGACTACGCCTGGAATCCCTACTACGGCACCTGGCAGGTCCCCGGCA

841   TCGCACTGCCCAAGGCGCAGCTGTCGCCGGCGGCCGTCGAGATCGGCCGGACCTCACGGA
                            SalI
  901   GCACCGTCGCCGACCTCGCCCGTCGCACCGTCGACGAGGGGTACGGCGTCTATCTGACGT

961   ACAACCTCGACGGCGGCGATCGCACCGCCGACGTCTCCGCGTTCACCAGGGAGCTGTACG

1021   GCAGCGAGGCGGTCCGGACGCCGTAGGGGCGTCGGGGCCTGCCGTCAGTCCAGTACGAAG
                                                              BamHI
 1081   GTGCCGCCGGCGGTGGTCGCCTGGCCGTGCCCGAAAGCGGCCGCCGGCGTCCAGGATCC
```

FIG. 8 pUC13

```
   1 GCGCCCAATACGCAAACCGCCTCTCCCCGCGCGTTGGCCGATTCATTAATGCAGCTGGCA
  61 CGACAGGTTTCCCGACTGGAAAGCGGGCAGTGAGCGCAACGCAATTAATGTGAGTTAGCT
 121 CACTCATTAGGCACCCCAGGCTTTACACTTTATGCTTCCGGCTCGTATGTTGTGTGGAAT
 181 TGTGAGCGGATAACAATTTCACACAGGAAACAGCTATGACCATGATTACGCCAAGCTTGG
 241 GCTGCAGGTCGACTCTAGAGGATCCCCGGGCGAGCTCGAATTCACTGGCCGTCGTTTTAC
 301 AACGTCGTGACTGGGAAAACCCTGGCGTTACCCAACTTAATCGCCTTGCAGCACATCCCC
 361 CTTTCGCCAGCTGGCGTAATAGCGAAGAGGCCCGCACCGATCGCCCTTCCCAACAGTTGC
 421 GCAGCCTGAATGGCGAATGGCGCCTGATGCGGTATTTTCTCCTTACGCATCTGTGCGGTA
 481 TTTCACACCGCATATGGTGCACTCTCAGTACAATCTGCTCTGATGCCGCATAGTTAAGCC
 541 AGCCCCGACACCCGCCAACACCCGCTGACGCGCCCTGACGGGCTTGTCTGCTCCCGGCAT
 601 CCGCTTACAGACAAGCTGTGACCGTCTCCGGGAGCTGCATGTGTCAGAGGTTTTCACCGT
 661 CATCACCGAAACGCGCGAGACGAAAGGGCCTCGTGATACGCCTATTTTTATAGGTTAATG
 721 TCATGATAATAATGGTTTCTTAGACGTCAGGTGGCACTTTTCGGGGAAATGTGCGCGGAA
 781 CCCCTATTTGTTTATTTTTCTAAATACATTCAAATATGTATCCGCTCATGAGACAATAAC
 841 CCTGATAAATGCTTCAATAATATTGAAAAAGGAAGAGTATGAGTATTCAACATTTCCGTG
 901 TCGCCCTTATTCCCTTTTTTGCGGCATTTTGCCTTCCTGTTTTTGCTCACCCAGAAACGC
 961 TGGTGAAAGTAAAAGATGCTGAAGATCAGTTGGGTGCACGAGTGGGTTACATCGAACTGG
1021 ATCTCAACAGCGGTAAGATCCTTGAGAGTTTTCGCCCCGAAGAACGTTTTCCAATGATGA
1081 GCACTTTTAAAGTTCTGCTATGTGGCGCGGTATTATCCCGTATTGACGCCGGGCAAGAGC
1141 AACTCGGTCGCCGCATACACTATTCTCAGAATGACTTGGTTGAGTACTCACCAGTCACAG
1201 AAAAGCATCTTACGGATGGCATGACAGTAAGAGAATTATGCAGTGCTGCCATAACCATGA
1261 GTGATAACACTGCGGCCAACTTACTTCTGACAACGATCGGAGGACCGAAGGAGCTAACCG
1321 CTTTTTTGCACAACATGGGGGATCATGTAACTCGCCTTGATCGTTGGGAACCGGAGCTGA
1381 ATGAAGCCATACCAAACGACGAGCGTGACACCACGATGCCTGTAGCAATGGCAACAACGT
1441 TGCGCAAACTATTAACTGGCGAACTACTTACTCTAGCTTCCCGGCAACAATTAATAGACT
1501 GGATGGAGGCGGATAAAGTTGCAGGACCACTTCTGCGCTCGGCCCTTCCGGCTGGCTGGT
1561 TTATTGCTGATAAATCTGGAGCCGGTGAGCGTGGGTCTCGCGGTATCATTGCAGCACTGG
1621 GGCCAGATGGTAAGCCCTCCCGTATCGTAGTTATCTACACGACGGGGAGTCAGGCAACTA
1681 TGGATGAACGAAATAGACAGATCGCTGAGATAGGTGCCTCACTGATTAAGCATTGGTAAC
1741 TGTCAGACCAAGTTTACTCATATATACTTTAGATTGATTTAAAACTTCATTTTTAATTTA
1801 AAAGGATCTAGGTGAAGATCCTTTTTGATAATCTCATGACCAAAATCCCTTAACGTGAGT
1861 TTTCGTTCCACTGAGCGTCAGACCCCGTAGAAAAGATCAAAGGATCTTCTTGAGATCCTT
1921 TTTTTCTGCGCGTAATCTGCTGCTTGCAAACAAAAAAACCACCGCTACCAGCGGTGGTTT
1981 GTTTGCCGGATCAAGAGCTACCAACTCTTTTTCCGAAGGTAACTGGCTTCAGCAGAGCGC
2041 AGATACCAAATACTGTCCTTCTAGTGTAGCCGTAGTTAGGCCACCACTTCAAGAACTCTG
2101 TAGCACCGCCTACATACCTCGCTCTGCTAATCCTGTTACCAGTGGCTGCTGCCAGTGGCG
2161 ATAAGTCGTGTCTTACCGGGTTGGACTCAAGACGATAGTTACCGGATAAGGCGCAGCGGT
2221 CGGGCTGAACGGGGGGTTCGTGCACACAGCCCAGCTTGGAGCGAACGACCTACACCGAAC
2281 TGAGATACCTACAGCGTGAGCTATGAGAAAGCGCCACGCTTCCCGAAGGGAGAAAGGCGG
2341 ACAGGTATCCGGTAAGCGGCAGGGTCGGAACAGGAGAGCGCACGAGGGAGCTTCCAGGGG
2401 GAAACGCCTGGTATCTTTATAGTCCTGTCGGGTTTCGCCACCTCTGACTTGAGCGTCGAT
2461 TTTTGTGATGCTCGTCAGGGGGCGGAGCCTATGGAAAAACGCCAGCAACGCGGCCTTTT
2521 TACGGTTCCTGGCCTTTTGCTGGCCTTTTGCTCACATGTTCTTTCCTGCGTTATCCCCTG
2581 ATTCTGTGGATAACCGTATTACCGCCTTTGAGTGAGCTGATACCGCTCGCCGCAGCCGAA
2641 CGACCGAGCGCAGCGAGTCAGTGAGCGAGGAAGCGGAAGA
```

FIG. 9

EXPRESSION VECTOR FOR THE REGULATABLE EXPRESSION OF FOREIGN GENES IN PROKARYOTES

DESCRIPTION

The present invention is concerned with an expression vector for the regulatable expression of foreign genes in procaryotes.

Expression vectors are needed for the expression of proteins in procaryotes. Apart from the gene of the protein to be expressed, such vectors must also contain regulation sequences which make possible the transcription and translation processes in the cells used for the protein production. Insofar as expression is to be carried out in procaryotes, such regulation sequences originate from procaryotes and contain, for example, sequences of promoters, operators and ribosomal binding points. Usually, such regulation sequences are present in a vector, for example the plasmid pBR 322 or a derivative thereof, in front the gene. Besides the previously described regulation sequences, these vectors also contain a replication origin and a marker for the selection of the plasmid, for example tetracycline resistance, ampicillin resistance, kanamycin resistance and the like.

The DNA unit, which recognizes RNA polymerase dependent upon the DNA and is transferred into the messenger RNA, is referred to as a transcription unit. Such a transcription unit consists of recognition sequences for the DNA-dependent RNA polymerase, recognition sequences for the initiation of the ribosomal function (Shine-Dalgarno sequence), the start codon ATG, a stop codon and termination sequences at which the transcription is terminated. Certain genes, namely those the gene products of which do not remain localized in the cytoplasm but rather are secreted into the periplasm or into the outer membrane, can, in addition, contain yet other recognition sequences. Such a recognition sequence for the excretion of proteins is called a signal sequence. A signal sequence contains characteristically charged segments, hydrophobic regions and hydrophilic regions and a signal sequence cleavage site (see the review article, Mechanism of Protein Localisation, Microbiol. Reviews, 47, 314–344/1983).

Consequently, the following requirements are demanded of an expression vector:

a) it must contain a strong promotor,
b) fusions with foreign genes are to be easy to carry out; and
c) the promotor, including an attached foreign gene section, should be suitable to make possible a localisation of the protein not only in the cyto-plasm but also in the periplasm or in the medium.

It is known that the extent of the expression of the foreign gene depends substantially upon the promotor. In order to assess whether a particular promotor is especially suitable for the expression of foreign genes, it does not depend, however, solely upon the amount of the foreign protein produced per cell but very often it is desirable that the gene product is not synthesized during the whole of the growth phase but only over a particular period of time and preferably in the late growth phase. This is particularly desirable in the case of the expression of gene products which, when they are present in large amounts, are either toxic to the cells or inhibit the growth of the cells. Therefore, it is often necessary to suppress the activity of a promotor at the beginning of the fermentation phase so that initially an extensive biomass is produced. Subsequently, by suitable means, the promotor should be stimulated and the expression of the foreign gene can take place.

Promotors known for this purpose include, for example, the lac promotor, the trp promotor and the $\lambda$-$P_L$-promotor. However, these promotors are not very suitable for a large-scale production of heterologous proteins. It is known that the lac promotor is inactivated by glucose but not completely enough to prevent the synthesis of "toxic" proteins. The trp promotor is also not an especially suitable promotor for large-scale production. Quite apart from the fact that the use of high tryptophane concentrations for the repression makes the fermentation considerably more expensive, it has been found that tryptophane does not make possible a complete repression so that here, too, disturbing expression can take place during the initial phase of the fermentation. The $\lambda$-$P_L$-promotor is also not suitable for a large-scale fermentation. The repression mechanism here takes place by the binding of a thermolabile repressor to an operator present behind the promotor at 32° C. The repressor is inactivated by increasing the temperature to 42° C., the transcription thereby being made possible. For large-scale production, which involves the use of fermentation volumes of 50 to 100 m³, such an increase of the temperature involves great difficulties. Furthermore, it has been found that the induction of the $\lambda$-$P_L$-promotor must take place in an early growth phase so that the biomass necessary for a biotechnical large-scale production cannot be achieved.

Therefore, it is an object of the present invention to overcome the above-described difficulties and to provide an expression vector for the regulatable expression of foreign genes in prokaryotes.

Thus, according to the present invention, there is provided an expression vector which consists of a DNA vector which, as regulation sequence, contains the promotor/operator region and the initiation point of the translation of the mgl operon. The terms "expression vector" or "vector," as used herein, refer to recipient DNA molecules which contain an origin of replication and a marker so as to show its presence in a host cell. A foreign gene may be introduced into the vector, if desired.

When the expression vector contains at least one foreign gene which is under the expression control of the mgl operon regulation sequences, its expression can be positively or negatively regulated via the mgl promotor. However, the foreign gene can also be introduced later.

The mgl promotor contained in the expression vector according to the present invention is a part of the mgl operon which, besides the promotor, also contains 4 structural genes, mglA, mglB, mglE and mglC, which are subject to control by the mgl promotor. The mglB gene hereby codes for a galactosidase binding protein of 33,000 Dalton and mglA, mglC and mglE each code for membrane-bound proteins. Thus, proteins are expressed by the mgl operon which are responsible for the transport of galactose from the medium into the bacterial cell.

For the production of the vector according to the present invention, the mgl operon can, in principle, be isolated from the genome of a cell which is able to utilise galactose provided from the outside, for example from *Salmonella typhimurium*, DSM 554, or from *Escherichia coli*, MC 4100 (DSM 4090) (J. Biol. Chem., 258, 10853–10855/1983; J. Bacteriol., 153, 408–415/1983).

The isolation of the mgl operon from *Salmonella typhimurium* can, according to the present invention, take place in such a manner that the genomic DNA is cleaved with EcoRI and a 6.3 kb sized fragment is isolated which is cloned in the usual way and can subsequently be expressed (cf. in this regard, J. Bacteriol., 163, 37–85/1985, as well as the literature cited therein). From the plasmid pNM 506 cited in this literature reference, there can be split out, by cleavage with EcoRI and BamHI, an approximately 900 bp-sized fragment which is then isolated. From the DNA sequence of this fragment was determined the sequence beginning immediately after the EcoRI recognition sequence (see FIG. 1 of the accompanying drawings). At position 705 to 707 is present the start codon ATG. Five nucleotides before, there lies the nucleotide sequence GGAG recognisable as Shine-Dalgarno sequence. This fragment contains the mg1 promotor which, however, only represents a part of this DNA sequence.

In contradistinction to previously known regulation systems, the mg1 promotor can be almost completely repressed with glucose and other catabolyte-repressing sugars, for example fructose or glucose-6-phosphate. Thus, with the use of the mg1 promotor according to the present invention, it is possible to control gene expression in an especially simple way. For example, in case of the fermentation, glucose as a source of carbon can be added in a certain amount. After the glucose has been used up, the expression commences, in which case another source of carbon must then be added which does not act catabolyte-repressingly, for example glycerol or succinate. The promotor activity can be still further increased by the further addition of fucose. The repression by glucose constitutes a factor of about 100.

The DNA vector which forms the basis of the expression vector according to the present invention can be a plasmid, a phage genome or also a shuttle vector which is expressible in gram-positive or gram-negative bacteria and especially in Enterobacteria. As expression vectors there are suitable the vectors which can be multiplied in the mentioned bacteria. Examples include pBR vectors, such as pBR 322, pUC vectors, such as pUC 18, as well as the phages lambda and ml3 and the derivatives thereof. For the insertion of the foreign gene to be expressed, the expression vector preferably contains a polylinker. Such a polylinker is incorporated according to known methods into the vector behind the regulation sequences. A preferred polylinker contains one or more restriction cleavage points which do not occur or only occur rarely in the plasmid or phage genome used. With the appropriate restriction enzyme(s), the vector is then cleaved and the foreign gene, which is either cleaved with the same restriction endonuclease or both ends of which are so altered in known manner that they also match with the cleavage point in question, is ligated in.

In order to determine from the very beginning the localization of the gene product in the host cell, between the regulation sequences and the foreign gene there can be inserted the DNA sequence for a signal peptide. According to the present invention, there is preferably used the DNA sequence for the signal peptide of the mg1B protein which brings about a localization in the periplasma (J. Biol. Chem., 258, 10853–10855/1983). However, in its place, there can also be used another known signal sequence or a consensus sequence (Nature, 321, 706–708/1986). Such consensus sequences can be determined amongst one another by comparison of known signal sequences. Without signal peptide, the foreign gene product remains in the cytoplasm.

According to a first embodiment of the present invention, an expression vector according to the present invention preferably contains the sequence which is illustrated in FIG. 1 of the accompanying drawings and includes the mg1 promotor or a sequence is hybridized therewith under standard conditions. This can also be a DNA sequence shortened in comparison with the sequence of FIG. 1 but which must still contain the whole mg1 promotor. By standard conditions are to be understood hybridization conditions such as are described by T. Maniatis, Molecular Cloning CSH, 383–389/1982.

The expression product of an attached foreign gene is then localized in the cytoplasm. If excretion into the periplasm is desired, according to another preferred embodiment, the mg1B signal sequence, which is illustrated in the lower part of FIG. 1 (signal sequence of the mg1B sequence) is attached to the preceding sequence.

The present invention also provides the plasmids M13mg1506 and M13mg1EcoK which contain a DNA sequence corresponding to an about 900 bp EcoRI/BamHI fragment of the plasmid pNM506 (FIG. 1), as well as, in the case of M13mg1EcoK, a polylinker sequence (4×EcoK cassette, Nucleic Acids Research, 13, 8561–8571/1985) inserted into the double-stranded, replicative form of the phage M13mp18 (sequence described in Gene, 33, 103–119/1985). According to the present invention, the plasmid M13mg1506 is produced by ligating a DNA sequence corresponding to the EcoRI/BamHI fragment of the plasmid pNM506 into the double-stranded, replicative form of the phage M13mp18, also cleaved with EcoRI and BamHI. The process according to the present invention for the production of the plasmid M13mg1EcoK includes ligating in of a DNA sequence corresponding to the EcoRI/BamHI fragment of the plasmid pNM506, together with a DNA sequence corresponding to the BamHI/EcoRI fragment from the plasmid M13K11 which contains four EcoK cleavage points (4×EcoK Cassette, Nucleic Acids Research, 13, 8561–8571/1985) which simplifies the carrying out of deletion mutagenesis in which a foreign gene can be introduced directly behind the operon sequence (Methods Enzymol., 100, 468–500/1983; Nucleic Acids Res., 10, 6487–6500/1982) and can function as polylinker for the insertion of any desired gene in the replicative form of the phage M13mp18 cleaved with EcoRI.

The use according to the present invention of a regulation sequence of the mg1 operon makes possible the expression of foreign genes regulatable by catalyte-repressing sugars, for example glucose, in which case it becomes possible also to produce on a large scale even gene products toxic for the expressed cells because the expression is made possible only in the late growth cycle after removal or fermentation of the sugar. It is thereby also possible to predetermine the later localization of the gene product, in which case a localization in the periplasm or even release of the gene product into the medium by the above-explained construction of the expression vector according to the present invention can be predetermined, for example by the use of a procaryote, which can give off substances into the medium, for example gram-positive bacteria or *Escherichia coli* mutants, such as are described, for example, in FEMS microbiol. Lett., 51, 411–416/1979 and J. Bact., 145, 1351–1358/1981. In this way, the necessity of cell digestion is avoided and it becomes possible to carry out the production of gene products which are not toxic for the host cell continuously, in which case the product can be continuously obtained from the medium.

BRIEF DESCRIPTION OF THE DRAWINGS

FIG. 1 shows the sequence of the EcoRI/BamHI fragment of plasmid pNM506, which contains the mg1 promotor and the mg1B signal sequence. DNA and amino acid sequences are provided.

FIG. 7 presents the nucleotide sequence of vector pUC18.

FIG. 8 shows the sequence of the Endo-β-N-acetylglucosaminidase H gene.

FIG. 9 presents the nucleotide sequence of vector pUC13.

The following Examples are given for the purpose of illustrating the present invention:

EXAMPLE 1

Isolation of the mg1 Promotor Operator Region

A 897 base pair-sized fragment (FIG. 1) is obtained from the plasmid pNM506 (J. Bacteriol., 163, 37–45/1985) by cleavage with EcoRI and BamHII. This fragment contains the promotor-operator region of the mg1 operon. It is ligated into the double-stranded replicative form of the phage M13mp18 (sequence cf. Gene, 33, 103–119/1985), which has also been cleaved with EcoRI and BamHI, with the help of T4 DNA ligase. The resulting plasmid has the designation M13mg1506.

Figure 2:
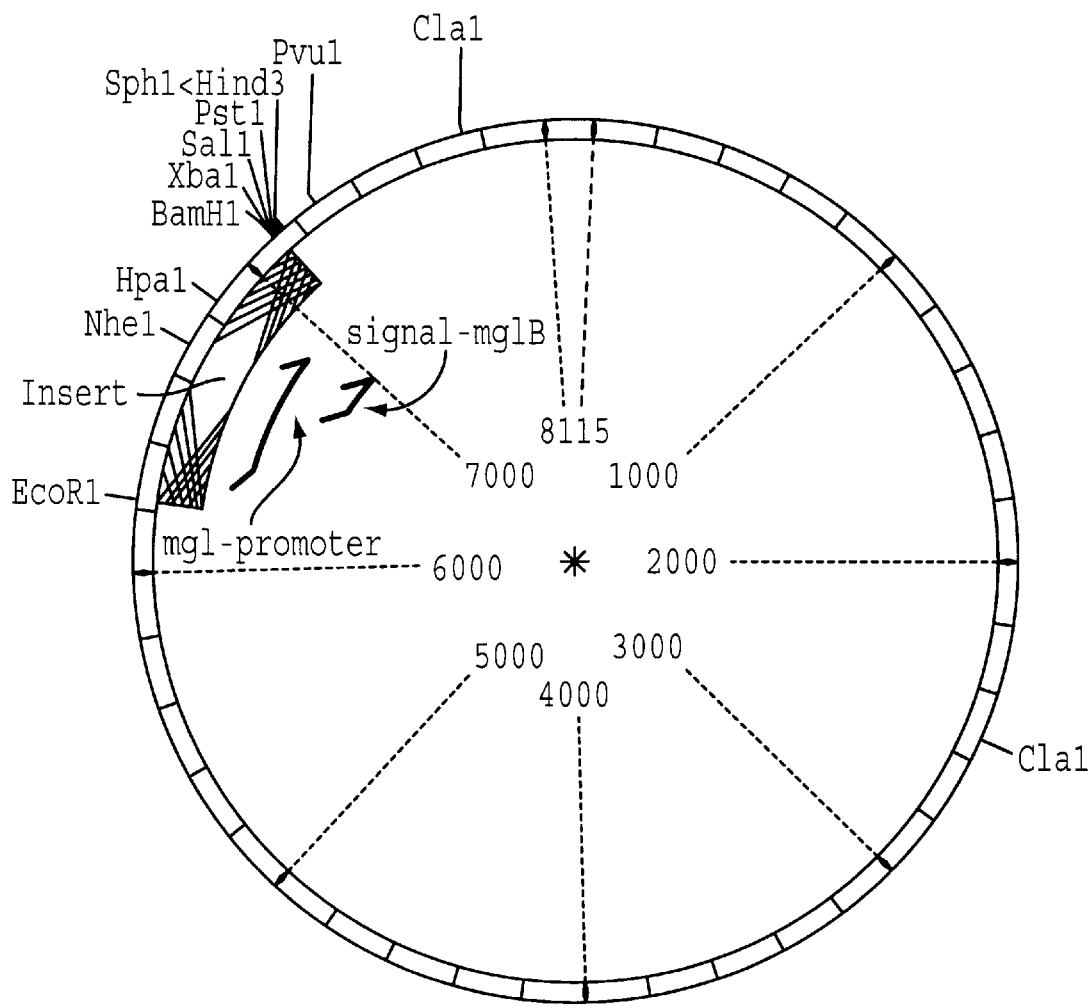
FIG. 2 shows the restriction map of M13mg1506.
Figure 3:
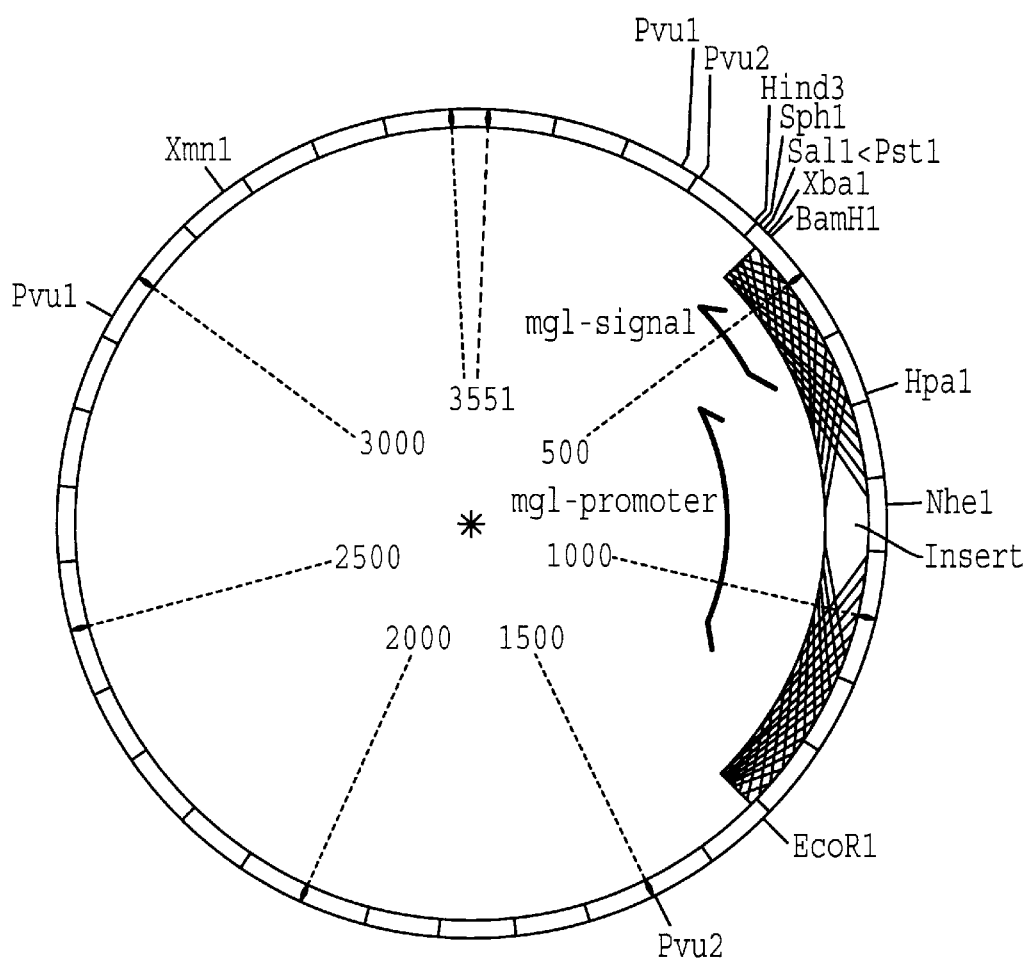
FIG. 3 depicts a restriction map of plasmid pUC18. The EcoRI-BamHI fragment contains the mg1 promotor.

In an analogous way, there is produced an equivalent plasmid in that the plasmid pUC18 (FIG. 7) is also cleaved with EcoRI and BamHI and the said fragment is there used (FIG. 3).

These two vectors serve as source for the DNA fragment with mg1 promotor and possibly additionally with mg1B signal sequence for the construction of vectors which, under the control of the mg1 promotor, can express foreign genes.

EXAMPLE 2

Figure 4:
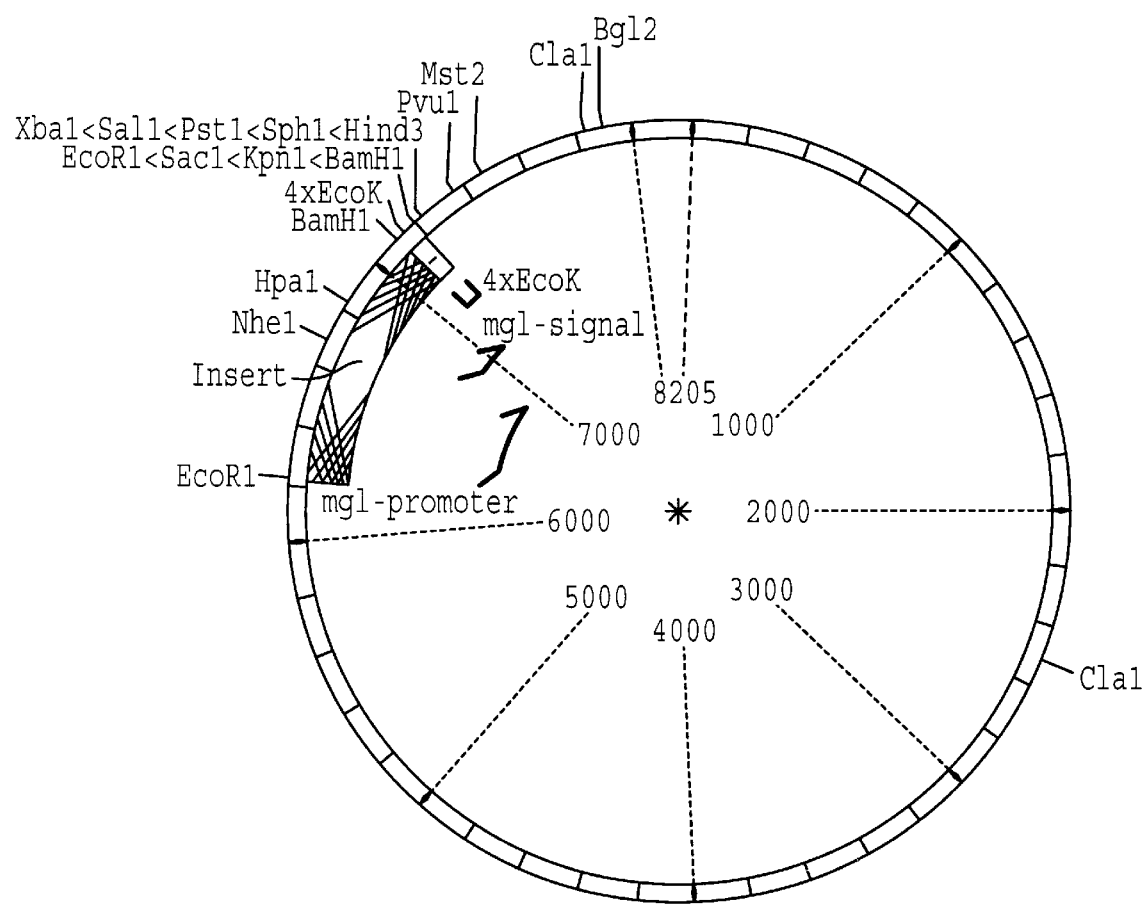
FIG. 4 presents the restriction map of M13mg1EcoK.

Construction of a Universal Vector with mg1 Promotor into which Foreign Genes can be Incorporated A DNA fragment from M13K11, which carries four EcoK cleavage points and on the ends a BamHI and an EcoRI cleavage point (4×EcoK cassette) (described in Nucleic Acids Research, 13, 8561–8571/1985), is ligated, together with the EcoRI, BamHI fragment from pNM506 (Example 1), into a vector M13mp18 cleaved with EcoRI, the vector M13mg1EcoK (FIG. 4) thereby being obtained. This vector possesses a polylinker region with the cleavage points KpnI, SacI, HindIII, SphI, PstI, SalI and XbaI, into which any desired foreign genes can be introduced.

EXAMPLE 3

Vector for the Expression of Endo-β-N-acetylglucos-aminidase H (endo H)

The N-terminal part of the endo H gene (FIG. 8, length 609 bp) defined by the cleavage points EcoRI and SalI (Journal of Biological Chemistry, 259, 7577–7583/1984) is isolated from the plasmid pEH 7'.

Figure 5:
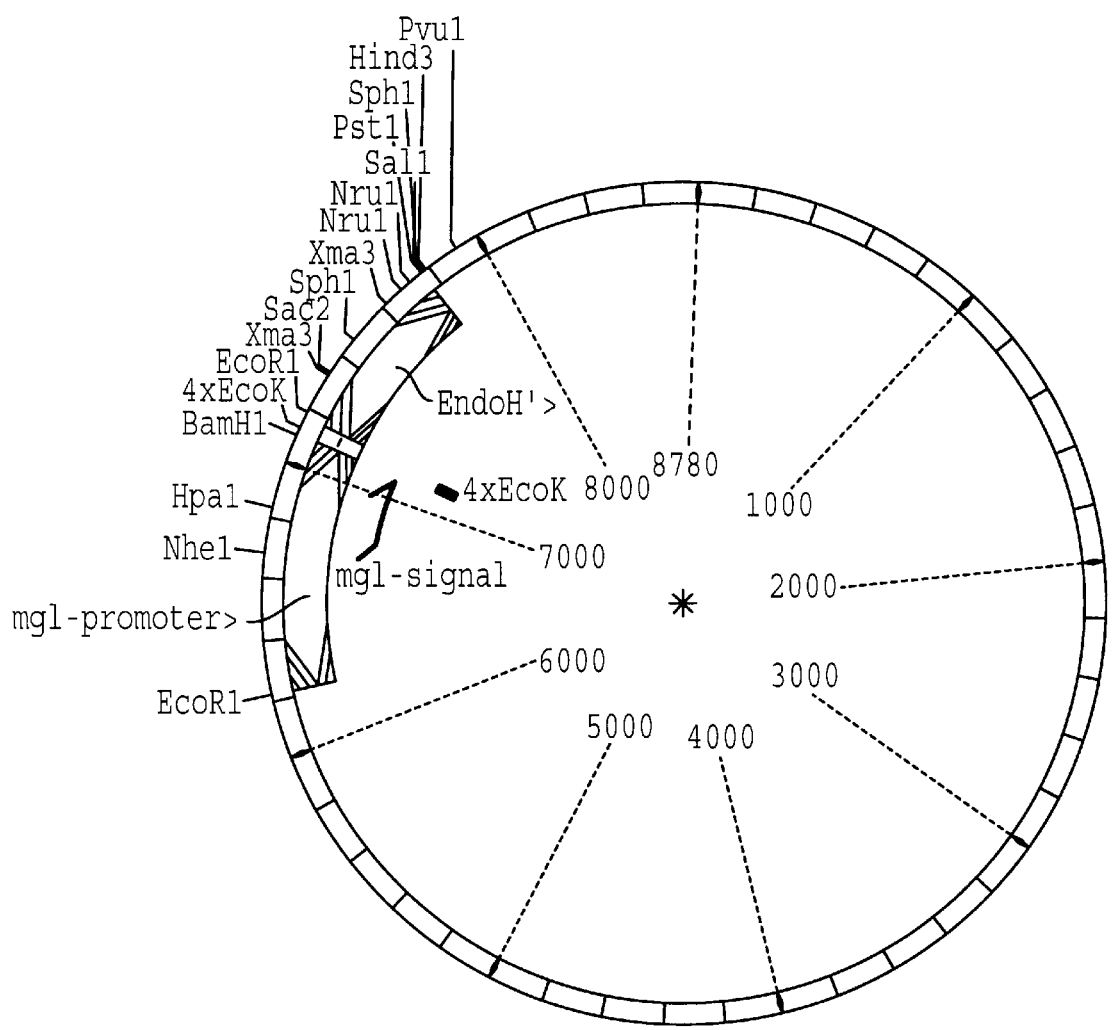
FIG. 5 shows the restriction map of M13mg1506, which contains four copies of the EcoK cassette and an EcoRI/SalI fragment containing the N-terminal part of the Endo-H gene.

The fragment obtained from M13mg1506 (Example 1) by cleavage with BamHI and SalI, the above-described EcoRI-SalI fragment, as well as the 4×EcoK cassette described in Example 2 (as EcoRI-BamHI fragment) are ligated with T4 ligase, the construction according to FIG. 5 thereby resulting.

By in vitro mutagenesis (Methods Enzymol., 100, 468–500/1983; Nucleic Acids Research, 10, 6487–6500/1982) with a synthetic oligonucleotide of the sequence: 5' CCCCTGCTTC ACCGGGGCCA TGGTAGCTCC GGTTTT 3' there is obtained a fusion between the ATG of the mg1 promotor and the N-terminal part of the mature EndoH gene. Neither a signal sequence of mg1 nor of EndoH is hereby present. The clones which contain the desired deletion are identified via a screening with the above-described radioactively-labelled oligonucleotide as sample. From a clone identified by this screening, there is prepared the replicative DNA.

Figure 6:
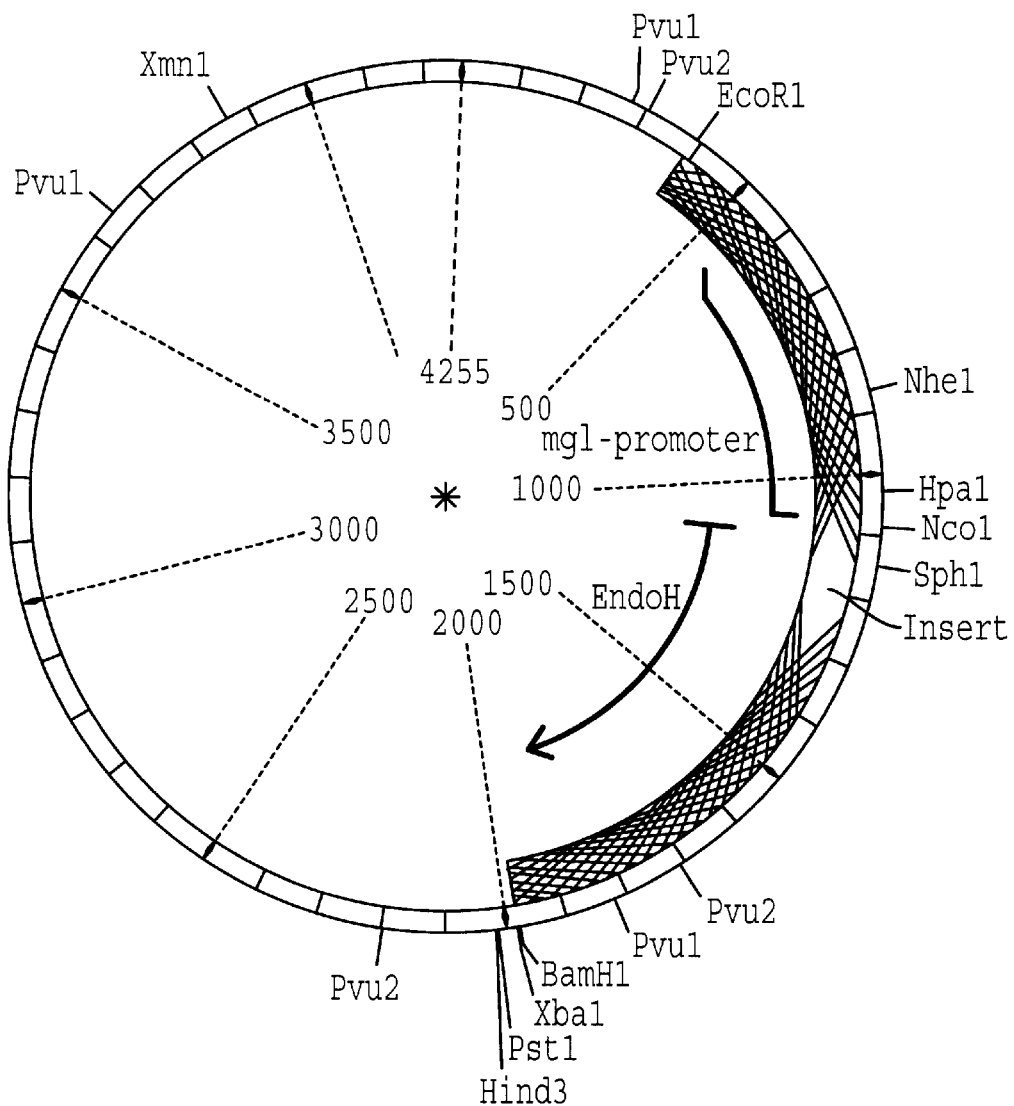
FIG. 6 shows the restriction map of pBT0103.

This DNA is cleaved with EcoRI and SphI. The fragment which hereby results (750 base pairs) is ligated with an SphI-BamHI fragment, which contains the residue of the endo H gene from SphI to over the end of the gene (J. Biol. Chem., 259, 7577–7583/1984), into a PUC13 vector cleaved with EcoRI and BamHI (sequence FIG. 9). A vector hereby results which carries the mg1 promotor gene, as well as the complete gene of EndoH (FIG. 6). This vector is designated pBT0103.

With the help of this plasmid, endoglycosidase H can be expressed in *Escherichia coli* HB101, DSM 1607. The expression can be controlled by the addition of glucose.

TABLE I

Culturing of *E. coli* HB101 with plasmid pBT0103 in LB medium (10 mg. trypton, 5 g. yeast extract, 5 g. sodium chloride per litre), with and without glucose.

| glucose | activity of EndoH (U/l. of medium |
|---------|-----------------------------------|
| 0%      | about 100                         |
| 0.1%    | about 10                          |
| 0.2%    | 0                                 |
| 0.4%    | 0                                 |

Analogous results are obtained when glucose-6-phosphate is used instead of glucose.

EXAMPLE 4

Vector with mg1 Promoter, mg1 Signal Sequence and Endo H Gene

The plasmid pBT0103 (Example 3) is cleaved with NcoI and a synthetic linker, which codes for the mg1 signal peptide (FIG. 1, Position 688–756), is introduced by ligation so that there is ensured a correct reading raster, as well as correct processing.

EXAMPLE 5

Vector with mg1 Promoter and β-galactosidase Gene Without Signal Sequence

The plasmid pBT0103 (Example 3) is cleaved with NcoI/PstI and the 3.3 kb-sized fragment hereby resulting is isolated.

Figure 10:
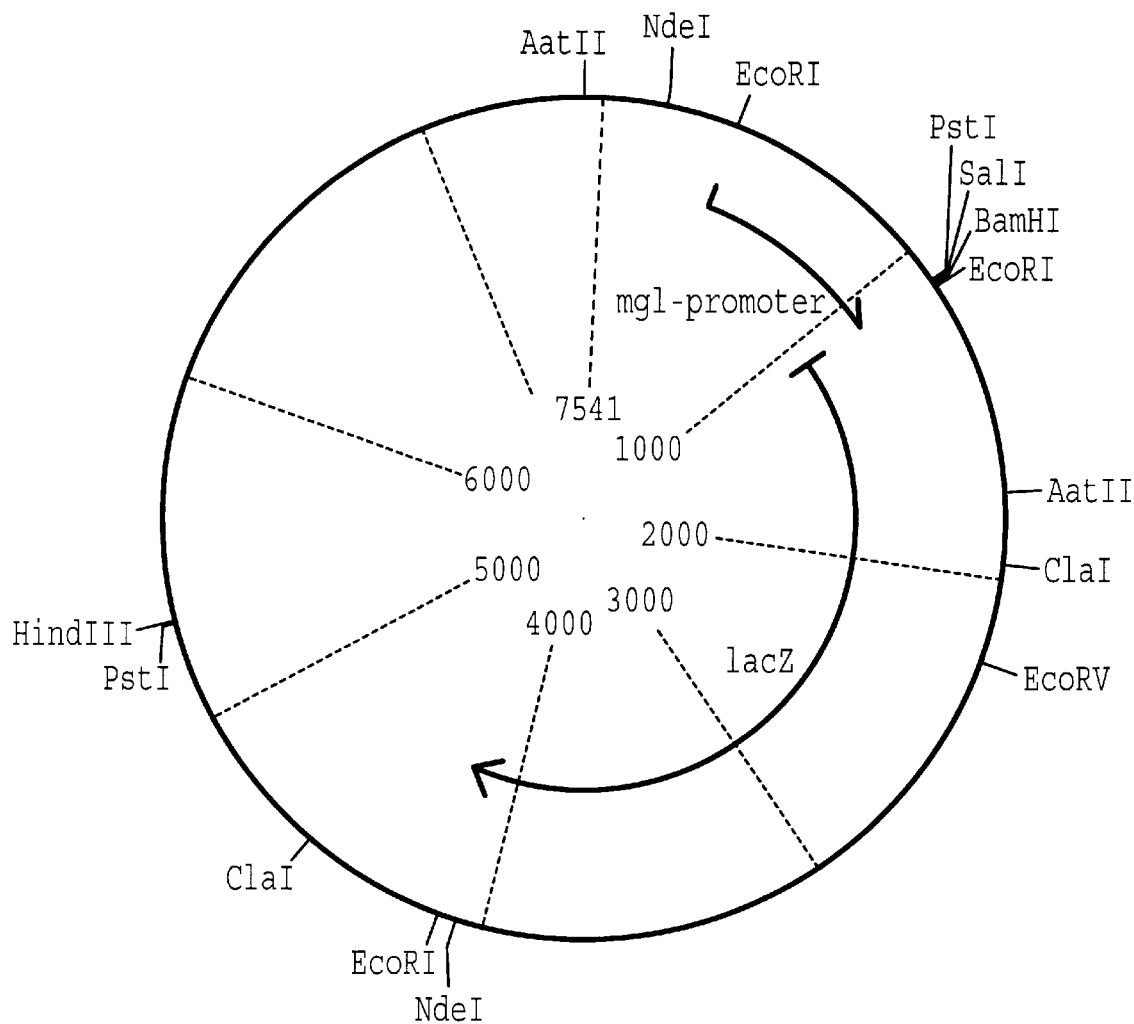
FIG. 10 is a restriction map of plasmid pPZ07mg1lac.

A BaHI/PstI fragment of about 5 kb of the plasmid pBT 117, DSM 3063 (described in European Patent Specification No. 0,180,225 A2), which contains the greater part of the lacZ gene, is prepared and, with the use of a synthetic linker of the sequence:

```
5' C ATG GTT ACG GAT TGC TGC AGG TCG ACG    3'
      ||| ||| ||| ||| ||| ||| ||| ||
3'     CAA TGC CTA ACG ACG TCC AGC TGC CTA G  5'
    NcoI                 PstI    SalI    BamHI
``` is ligated with the 3.3 kb fragment, a plasmnid thereby being obtained in which the reading frame of the lacZ is fused on to the ATG of the mg1 gene (pPZ07-mg1lac, FIG. 10). In the case of the introduction of the plasmid into *Escherichia coli* HB101, DSM 1607, there is observed an expression of β-galactosidase into the cytoplasmic fraction of the cell, which is controllable by glucose (see the following Table II).

TABLE II

| strain | β-galactosidase activity | |
|---|---|---|
| | LB medium | LB medium + 0.2% glucose |
| HB101 | 4900 | 4700 |
| HB101 × pPZ07-mg11ac | 31400 | 1700 |

(The β-galactosidase activity determination was carried out as described by J. H. Miller (1972), Experiments in molecular genetics, Cold Spring Harbor Press, Cold Spring Harbor, N.Y.).

EXAMPLE 6

Expression of Pen-G Amidase

The mg1 expression plasmid was used in order to express the periplasmic enzyme penicillin G amidase. The subcloning and the DNA sequence of penicillin G amidase are described in European Patent Specification No. 0,180,225 A2. The replicative form of the phage M13mg1506 (Example 1) was cleaved with HindIII and BamHI. The HindIII cleavage point was made smooth with polymerase I (Klenow fragment) and the four desoxyribonucleotide triphosphates before cleavage with BamHI.

From the plasmid pBT212, DSM 3058 (described in European Patent Specification No. 0,180,225 A2) was isolated a fragment of about 800 bp by cleavage with BamHI and AhaIII. This fragment is ligated into the previously described vector M13mg1506 opened with BamHI and HindIII. With the use of the oligonucleotide 5' ACTTGAC-GACTGCTCCGCGTGCGCGTGCGC 3' and of the single-stranded DNA of the phage M13, there can now be carried out a deletion mutagenesis. Details of this method are described in the handbook "Oligonucleotide-directed in vitro mutagenesis system", Amersham rpn 2322). Due to the deletion, there results an exact fusion between the mg1 signal sequence and the gene of the Pen-G amidase in such a manner that, into the protein which is transmiitted from the DNA, amino acid 23 of the mg1 signal peptide (FIG. 1) is fusioned with amino acid 27 of the Pen-G amidase. The clones which contain the desired deletion are identified via a screening with the above described radioactively-labelled oligonucleotide as sample (cf. Handbook loc. cit.). From a clone identified by the screening, there is prepared the replicative DNA (cf. Handbook loc. cit., M13 cloning and sequencing).

The DNA is cleaved with EcoRI and EcoRV and the approximately 1 kb-sized DNA fragment isolated. This DNA fragment is ligated into the vector pBT212 cleaved with EcoRI and EcoRV and the coding region of the Pen-G amidase thereby brought under the regulation control of the mg1 promotor.

EXAMPLE 7

Expression and Secretion of Penicillin G Amidase (PenG) via mg1 Promotor and mg1 Signal Peptide The plasmid pBTE1–11 (European Patent Specification No. 0,180,225 A2, DSM 3061) contains the PenG gene. By cleavage with the restriction endonucleases ClaI and SphI, there can be obtained a 182 bp sized DNA fragment, which includes the N-terminal region of the PenG gene, including the start of the mature PenG. This fragment is ligated into the vector M13mg1EcoK (FIG. 4) cleaved with AccI-SphI. By in vitro mutagenesis, as described in Example 3, with a synthetic oligonucleotide of the sequence: 1 ACTTGAC-GAC TGCTCCGCGT GCGCGTG 27 there is obtained a fusion between the end of the mg1B signal sequence and the start of the mature PenG. The sequence coding for the signal peptide of the PenG is absent. The clones which contain the desired deletion are identified via a screening with the above-described radioactively-labelled oligonucleotide as hybridising probe. Replicative, double-stranded DNA is prepared from these clones.

This DNA is cleaved with EcoRI and SphI. The resultant DNA fragment (812 bp) is ligated into the vector plasmid pUC18 cleaved with EcoRI and SphI. After the transformation of *Escherichia coli* HB101, plasmid DNA is prepared from a correct clone. This DNA is cleaved with SphI and HindIII and ligated with a DNA fragment of 3000 bp size which has been obtained from pBTE1–11 by cleavage with SphI and HindIII and contains the missing C-terminal region of the PenG gene.

Figure 11:
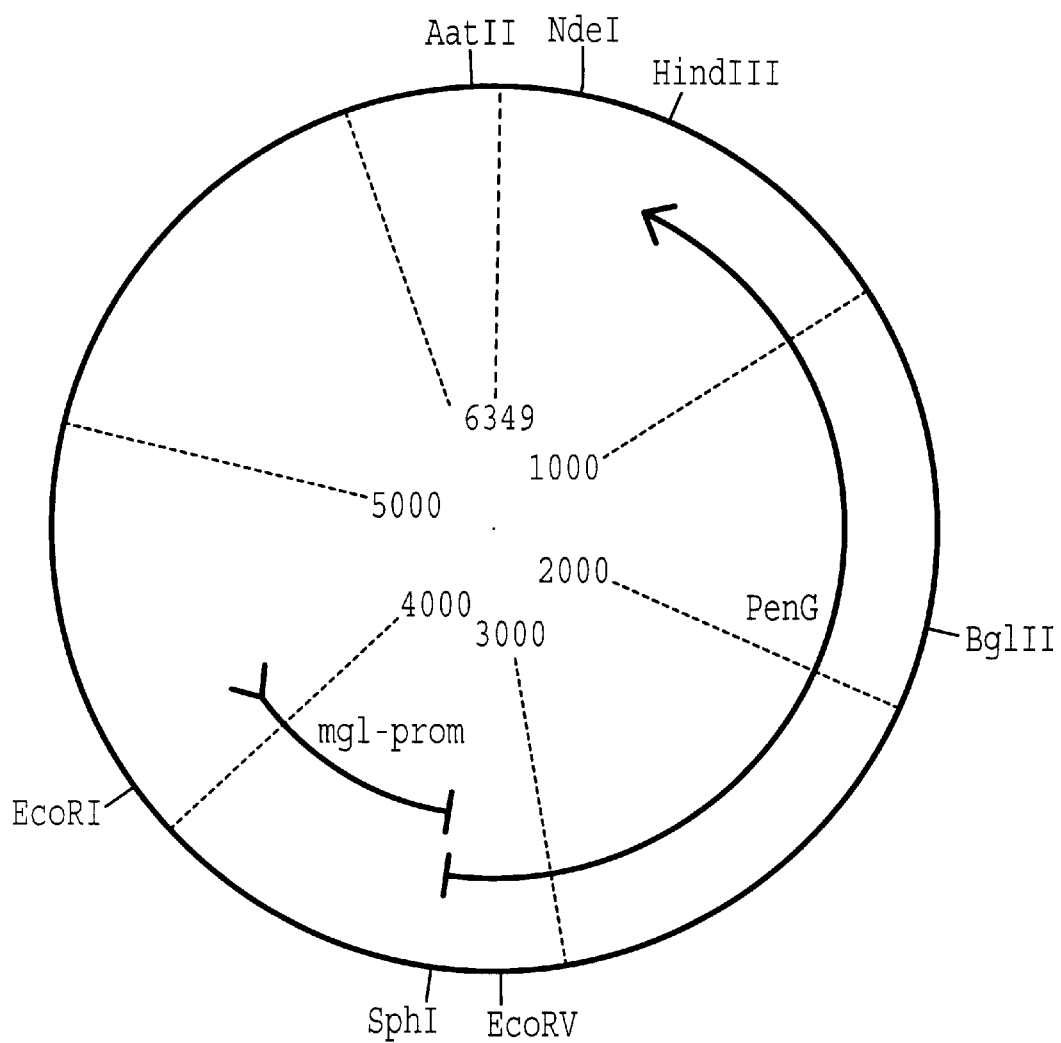
FIG. 11 is a restriction map of plasmid pPZ07mg1penG.

The plasmid thereby obtained, pPZ17-mg1penG (FIG. 11), contains the gene section coding for the mature PenG fusioned on to the mg1B signal sequence. The expression of this fusion gene is controlled via the mg1 promotor and is glucose-dependent (see the following Table III). Expressed PenG is secreted via the mg1B signal peptide into the periplasynic space and is there processed to give the active enzyme.

TABLE III

| | PenG activity (mU/A 420 cell density) | |
|---|---|---|
| strain | LB medium | LB medium + 0.4% glucose |
| HB101 × pUC18 | 0 | n.d. |
| HB101 × pPZ07-mglpenG | 20.9 | 0.8 |
| HB101 × pBT E1-11 | 1.7 | n.d. | n.d. = not determined (The PenG enzyme activity was determined with 2-nitro-5-phenylacetaininophenylacetic acid as colour substrate as described by C. Kutzbach and E. Rauenbusch, Hoppe-Seyler's Physiol. Chem., Vol. 354, 45–53/1974).

For the removal of the tac promotor present in the plasmid pBT212, the plasmid is cleaved with BamHI and EcoRI, the ends made smooth with DNA polymerase (Klenow fragment) and the four desoxyribonucleotide phosphates and religated.

In this plasmid, the expression of the Pen-G amidase is subject to the catabolite-repressing control and is discharged into the periplasma with the help of the mg1-B signal sequence.

What is claimed is:

1. An expression vector comprising a regulation sequence consisting essentially of a promoter/operator region of an *E. coli* or *S. typhimurium* mg1B operon up to but not including the ATG codon which is the initiation point of translation, wherein said expression vector does not include any sequences which code for mature mg1B protein.

2. The expression vector of claim 1, further comprising at least one gene which codes for a heterologous protein, expression of which is controlled by said regulation sequence, wherein said foreign gene is operably linked to said regulation sequence.

3. The expression vector of claim 1, comprising a plasmid or phage genome.

4. The expression vector of claim 1, comprising a bacterial shuttle vector.

5. The expression vector of claim 2, wherein said at least one gene is positioned in a polylinker sequence.

6. The expression vector of claim 2, further comprising a DNA sequence consisting essentially of a DNA sequence coding for mg1B signal peptide of FIG. 1, wherein said DNA sequence is positioned between said mg1 promotor/operator region and said gene coding for a heterologous protein, wherein said DNA sequence is operably linked to said gene.

7. The expression vector of claim 2, further comprising a DNA sequence consisting essentially of a consensus sequence for the mg1B signal peptide of FIG. 1, positioned between said mg1 promoter/operator region and said gene coding for heterologous protein, wherein said DNA sequence is operably linked to said gene.

8. The expression vector of claim 1, wherein said regulation sequence consists of nucleotides 1 to 704 of FIG. 1.

9. The expression vector of claim 6, wherein said regulation sequence and said DNA sequence for said mg1 signal peptide consist of nucleotides 1 to 773 of FIG. 1.

10. Isolated nucleic acid molecule consisting of the *E. coli* or *S. tymphimurium* mg1 promoter/operator region up to, but not including the ATG codon which is the initiation point of translation of an mg1 operon.

11. Isolated nucleic acid molecule consisting of nucleotides 1 to 704 of FIG. 1.

12. Isolated nucleic acid molecule consisting of nucleotides 1–773 of FIG. 1.

13. Plasmid M13mg1506.

14. Plasmid M13mg1EcoK.

* * * * *